United States Patent
Voigt et al.

(10) Patent No.: US 10,660,613 B2
(45) Date of Patent: May 26, 2020

(54) MEASUREMENT POINT DETERMINATION IN MEDICAL DIAGNOSTIC IMAGING

(71) Applicants: Siemens Healthcare GmbH, Erlangen (DE); Siemens Medical Solutions USA, Inc., Malvern, PA (US)

(72) Inventors: Ingmar Voigt, Erlangen (DE); Tommaso Mansi, Plainsboro, NJ (US); Helene C. Houle, San Jose, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 89 days.

(21) Appl. No.: 15/720,317

(22) Filed: Sep. 29, 2017

(65) Prior Publication Data

US 2019/0099159 A1 Apr. 4, 2019

(51) Int. Cl.
| | | |
|---|---|---|
| A61B 8/00 | (2006.01) | |
| G06T 7/62 | (2017.01) | |
| A61B 8/08 | (2006.01) | |
| A61B 6/03 | (2006.01) | |
| A61B 34/20 | (2016.01) | |
| A61B 5/055 | (2006.01) | |
| A61B 90/00 | (2016.01) | |

(52) U.S. Cl.
CPC ............. *A61B 8/466* (2013.01); *A61B 8/463* (2013.01); *A61B 8/483* (2013.01); *G06T 7/62* (2017.01); *A61B 5/055* (2013.01); *A61B 6/032* (2013.01); *A61B 8/462* (2013.01); *A61B 2034/2065* (2016.02); *A61B 2090/376* (2016.02); *A61B 2090/378* (2016.02); *A61B 2576/00* (2013.01); *G06T 2207/30048* (2013.01)

(58) Field of Classification Search
CPC ......... A61B 8/466; A61B 6/032; A61B 8/462; A61B 5/055; A61B 2034/2065; G06T 7/62; G06T 2207/30048
See application file for complete search history.

(56) References Cited

U.S. PATENT DOCUMENTS

| | | |
|---|---|---|
| 7,702,596 B2 | 4/2010 | Tu et al. |
| 8,532,352 B2 | 9/2013 | Ionasec et al. |
| 9,569,736 B1 | 2/2017 | Ghesu et al. |
| 9,730,643 B2 | 8/2017 | Georgescu et al. |

(Continued)

OTHER PUBLICATIONS

U.S. Appl. No. 15/661,429.

(Continued)

*Primary Examiner* — Qian Yang (57) ABSTRACT

For measurement point determination in imaging with a medical scanner, the user selects a location on the image. Rather than using that location, an "intended" location corresponding to a local boundary or landmark represented in the image is identified. The medical scanner uses the simple user interface to more exactly determine points for measurement. One or more rays are cast from the user selected location. The actual location is found by examining data along the ray or rays. For 2D imaging, the rays are cast in the plane. For 3D imaging, the ray is cast along a view direction to find the depth. The intensities along the ray or around the ray are used to find the actual location, such as by application of a machine-learnt classifier to the limited region around the ray or by finding intensities along the ray relative to a threshold.

19 Claims, 3 Drawing Sheets

(56) References Cited

U.S. PATENT DOCUMENTS

| | | | |
|---|---|---|---|
| 2011/0021915 A1* | 1/2011 | Feng | A61B 5/7267 600/443 |
| 2014/0152654 A1* | 6/2014 | Yoo | A61B 8/465 345/419 |
| 2015/0150460 A1* | 6/2015 | Krishnaswamy | A61B 1/07 600/408 |
| 2017/0103532 A1 | 4/2017 | Ghesu et al. | |
| 2017/0112473 A1* | 4/2017 | Samset | A61B 8/5246 |
| 2017/0361128 A1* | 12/2017 | Lachaine | A61N 5/1049 |

OTHER PUBLICATIONS

GE Healthcare. "4D Tee Transducer." ULTC-0271-09.13-EN-USDOC1449780. Downloaded Aug. 29, 2017.

Ghesu, Florin C., et al. "An artificial agent for anatomical landmark detection in medical images." International Conference on Medical Image Computing and Computer-Assisted Intervention. Springer International Publishing, 2016.

Ghesu, Florin C., et al. "Marginal space deep learning: Efficient architecture for detection in volumetric image data." International Conference on Medical Image Computing and Computer-Assisted Intervention. Springer, Cham, 2016.

Heimann, Tobias, et al. "Real-time ultrasound transducer localization in fluoroscopy images by transfer learning from synthetic training data." Medical image analysis 18.8 (2014): 1320-1328.

Miao, Shun, Z. Jane Wang, and Rui Liao. "A CNN regression approach for real-time 2D/3D registration." IEEE transactions on medical imaging 35.5 (2016): 1352-1363.

* cited by examiner

MEASUREMENT POINT DETERMINATION IN MEDICAL DIAGNOSTIC IMAGING

BACKGROUND

The present embodiments relate to medical diagnostic imaging. Many decisions in modern cardiology are based on quantitative measurements of anatomy, non-invasively derived from non-invasive imaging. Dimensions of the heart are different in normal function compared to open heart surgery.

Quantifying planar structures on two-dimensional (2D) images with contouring tools requires time consuming and diligent manual outlining. Convenient user interaction is important, particularly in an interventional setting where there may be limited degrees of freedom due to the many different activities occurring and/or limited user interface available in that setting (e.g., joystick control).

Recent advances in scanner technology enable three-dimensional plus time (3D+t) real-time ultrasound imaging of the heart. 3D imaging may make quantification even more difficult. 3D imaging is recognized to provide a better understanding of anatomical shape compared to traditional 2D imaging. On the other hand, the complexity of operating 2D ultrasound imaging is lower than 3D and often preferred in clinical practice. Also, for anatomical quantification, measurements are performed on 2D multi-planar reformatted or reconstruction (MPR) images, which are selected with additional user interfaces such as trackball controls or table side joystick controls.

With machine learning technologies, regular anatomical structures are efficiently and robustly modeled in fully-automatic or semi-automatic ways. Tackling anatomical variability may however be challenging, particularly in exceptional cases. Moreover, the machine-learnt technology is trained to provide specific segmentation and/or measurements, but users may want to define custom dimensions depending on their needs. Efficient workflows for deriving generic arbitrary quantitative information from 3D images in fast intuitive ways remain to be defined.

SUMMARY

By way of introduction, the preferred embodiments described below include methods, computer-readable media, and systems for measurement point determination in imaging with a medical scanner. The user selects a location on the image. Rather than using that location, an "intended" location corresponding to a local boundary or landmark represented in the image is identified. The medical scanner uses the simple user interface to more exactly determine points for measurement. One or more rays are cast from the user selected location. The actual location is found by examining data along the ray or rays. For 2D imaging (e.g., a MPR computed from 3D volume or a native or 2D scan image), the rays are cast within (i.e. parallel to) the plane. For 3D imaging, the ray is cast along a view direction towards the 3D volume to find the depth. The intensities along the ray or around the ray are used to find the actual location, such as by application of a machine-learnt classifier to the limited region around the ray or by finding intensities along the ray relative to a threshold.

In a first aspect, a method is provided for measurement point determination in imaging with an ultrasound scanner. An ultrasound image is three-dimensionally rendered from ultrasound data representing a volume of tissue of a patient onto a display. A user input device receives a position of a measurement caliper on the ultrasound image. A ray is defined along a view direction from the position of the measurement caliper into the volume. A depth along the ray is identified with a machine-learnt classifier based on input of ultrasound data from a sub-region of the volume limited to be around and include the ray. An image processor calculates a quantity as a function of the position of the measurement caliper and the depth. The quantity is output.

In a second aspect, a method is provided for measurement point determination in imaging with a medical scanner. A display displays a medical image mapped from intensities representing tissue of a patient. A user input device receives a position of a measurement caliper on the medical image. A ray extending from the position of the measurement caliper is defined. A location along the ray is identified based on the intensities from a sub-region limited to be around and include the ray. An image processor calculates a quantity as a function of the location. The quantity is output.

In a third aspect, a medical ultrasound system includes an ultrasound scanner configured to scan a volume of a patient, a user input device configured to receive an indication of a position on a volume rendered image of the volume of the patient, and an image processor. The image processor is configured to cast a ray from the position along a view direction, to select a location along the ray based on ultrasound data from the scan of the volume, and to generate a graphic indicating a point at the position and the location.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND SPECIFIC EMBODIMENTS

A user interface allows for inexact caliper placement by the user and automatically selects a refined position for quantification. 2D planar or 3D volume datasets are acquired with a medical scanner, such as with a computed tomography (CT), magnetic resonance (MR), ultrasound (e.g., TEE, TTE, ICE or another kind of transducer), or a combination of these modalities. Landmarks, contours or volumetric meshes are efficiently marked in a semi-automatic fashion either on a 3D volume visualization or a 2D planar (e.g., 2D MPR) image. The desired location is manually selected on a structure visualized as a surface in the volume rendering or a position in a 2D image. Structures nearby the mouse pointer are then selected or suggested, such as selecting a boundary of an organ or blood pool or selecting a discriminative anatomical landmark. The selected landmark points and contours may be visualized with an overlaid graphic, and measurements are calculated based on the points. The quantification may be performed with variation over time if 3D+t is available (e.g., 3D TEE, TTE or volume ICE in the case of cardiac ultrasound). The quantification may be related to other imaging, such as fusing multi-modality imaging to overlay anatomy and measurement graphics from ultrasound on fluoroscopy.

In one embodiment, landmarking and measurements are provided for 3D volume scans. User intuitive interactions with a 3D visualization of a volumetric medical image are provided. Points on organ parts visualized as surfaces (e.g. blood-tissue interfaces in the case of a 3D cardiac ultrasound scan) are identified. Instead of having to scroll through orthogonal MPRs until finding and verifying the desired 3D location, the user merely clicks on the 3D volume visualization. The image processor uses the selected position of the cursor upon the click and ray casting to place points, for example, on the endocardial wall, on the mitral valve annulus, leaflets, or any other structure visualized as an opaque surface, including medical implants. For 2D imaging (e.g., on an MPR), the user selects a position, which is then extrapolated to a boundary or landmark using ray casting. For tracing, the user's imprecise "scribbling" may be refined to be along a near boundary using ray casting. By limiting the search to data along the local rays, the refinement may occur in real time as compared to finding an entire boundary.

This approach allows designation of one or more locations directly on a volume rendering, reducing cumbersome MPR navigation to find each location. No MPR needs to be positioned to define depth and/or 3D point as points may be directly placed in a volume rendering. Contouring of arbitrary shapes on a volume rendering or 2D image (e.g., MPR) is facilitated, allowing the user to less precisely trace. Smooth interaction for advanced workflows is provided by the real-time landmark identification since the search is limited to a region proximate to the user selected position. Where machine learning is used to accurately find the landmark, the ray limited search region allows for more rapid identification of the landmark and/or allows training of a classifier that is generic to organs or parts of an organ. The same classifier may be applied to find boundaries regardless of the organ, making the landmark determination robust and versatile. Typically, extensive organ modeling operates at run times in orders of seconds, not necessarily at interactive frame rates. By reducing the search space around the defined ray, more rapid identification is provided. Further speedup is provided by operating on data in spherical coordinates prior to scan conversion and thus reducing the computation time.

Figure 1:
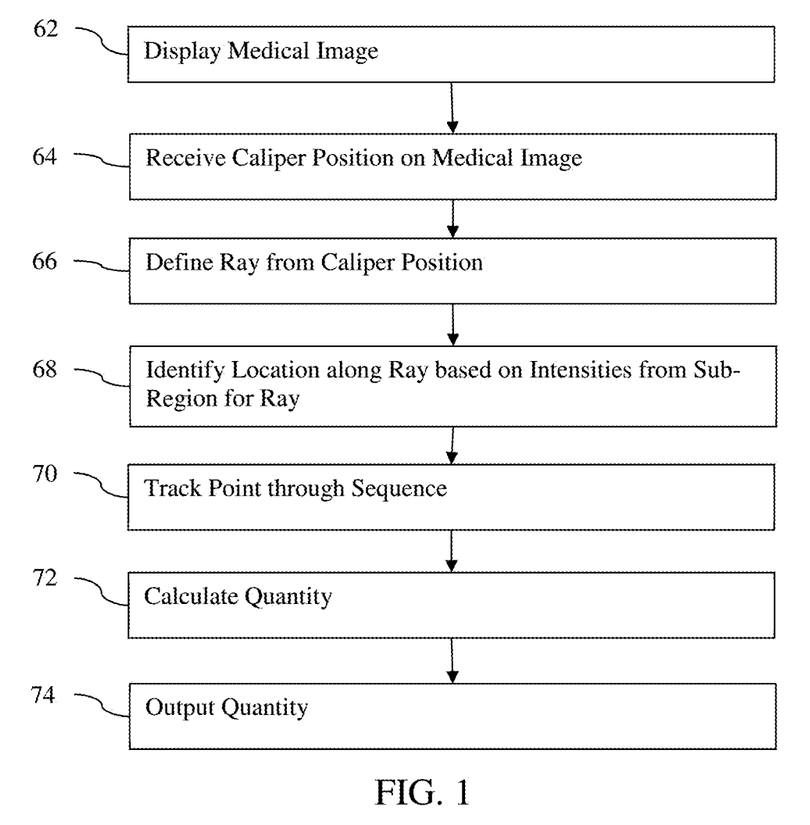
FIG. 1 is a flow chart diagram of an embodiment of a method for measurement point determination in medical imaging.

FIG. 1 shows one embodiment of a method for measurement point determination in imaging with a medical scanner, such as an ultrasound scanner. For quantification in medical imaging, the user selects a point or series of points. The image processor refines the selection based on a boundary or landmark search localized to the point, allowing for semiautomatic rapid point determination without requiring precise user entry. The point determination may be performed on a planar image or a volume rendering using ray casting from the user selected point.

The method is implemented by a medical diagnostic imaging system, a review station, a workstation, a computer, a PACS station, a server, combinations thereof, or another device for medical image processing. For example, the ultrasound system 10 or memory 14 and image processor 12 shown in FIG. 6 implements the method. Other systems or scanners may be used, such as CT or MR instead of ultrasound. In yet other embodiments, a computer, server, or workstation obtains medical image data from memory and a medical scanner is not provided.

The examples herein are provided for ultrasound imaging. In alternative embodiments, other medical modalities capable of medical imaging are used, such as magnetic resonance, computed tomography, positron emission tomography, single photon emission computed tomography, or x-ray.

The method is implemented in the order shown or a different order. A same data set representing a plane or volume is used for all of the acts 62-74. For a sequence of data sets, such as over a heart cycle, act 70 is performed instead of acts 64-68 after identifying the location in act 68 in one data set. The quantity is calculated and output as a function of time in acts 72 and 74. Alternatively, the acts 64-68 are repeated for each data set and corresponding time through the sequence.

The acts are performed either in real-time with scanning or in a post scan review. A freeze operation or selection of a given data set to use for measurement may be used. The user may view and interact with images while scanning, such as interacting with a frozen image where the point location is then tracked through the sequence in real-time.

Additional, different, or fewer acts may be performed. For example, act 70 is optional. As another example, scanning is performed to acquire the data used for the display in act 62. In yet another example, the quantity is calculated in act 72 without output in act 74. In one example, acts 72 and 74 are not performed, but instead a graphic or other highlight of a selected point or points are output with the image.

In act 62, an image processor or medical scanner displays a medical image. To display the medical image, a patient is scanned. For scanning, an ultrasound transducer is positioned adjacent, on, or within a patient. In one embodiment, a volume scanning transducer is positioned, such as a mechanical wobbler, a transesophageal echocardiogram (TEE) array, an intra-cardiac echocardiography (ICE) array, or multi-dimensional array. For planar or 2D imaging, a volume scanning transducer (e.g., for MPR) or a 2D imaging transducer (e.g., 1D array) may be used. For adjacent or on a patient, the transducer is positioned directly on the skin or acoustically coupled to the skin of the patient. For within the patient, an intraoperative, intercavity, ICE array, TEE array, or another transducer positionable within the patient is used to scan from within the patient.

The user may manually position the transducer, such as using a handheld probe or manipulating steering wires. Alternatively, a robotic or mechanical mechanism positions the transducer.

The volume region of the patient is scanned. Alternatively, a 2D or just a plane of the patient is scanned. An entire heart or portion of the heart may be scanned from the esophagus or through another acoustic window. Other organs or parts of a patient may be scanned. One or more objects, such as the heart, an organ, a vessel, fluid chamber, clot, lesion, muscle, and/or tissue are within the region. The array generates acoustic energy and receives responsive echoes.

One or more sets of ultrasound data are obtained. The ultrasound data corresponds to a displayed image (e.g., detected and scan converted ultrasound data), beamformed data, detected data, and/or scan converted data. The ultrasound data represents a region of a patient. Data for multiple planar slices may represent the volume region. Alternatively, a volume scan is used.

The ultrasound data is of any imaging mode, such as flow mode or B-mode. Flow mode includes Doppler or other estimates of motion (e.g., color or Doppler velocity or energy). The shape of a structure or spatial aspect may be reflected in B-mode data.

In act 62, a display device displays a medical image. The medical image is mapped from intensities representing tissue and/or other objects in the patient. The scanning provides intensities. For example, the intensities are B-mode or flow mode values from ultrasound scanning. As another example, the intensities are generated by beamforming prior to detection. After detection, the scalar values for the intensities may be scan converted, providing intensities in a different format. By mapping scalar values to a dynamic range and with an image gain, display values are generated as intensities. The medical image is a color or a gray-scale image. Cardiac imaging or imaging of other parts of the body may be provided.

In one embodiment, the medical image is a volume rendered image of a volume of tissue scanned by ultrasound. Using surface rendering, projection, path tracing, or other volume rendering technique, the data representing the volume is rendered to an image. An image processor (e.g., a graphics processing unit) renders the image on the display.

The image includes information from the entire volume or a non-planar portion of the volume. For example, the value of a given pixel is determined from multiple voxels along a line passing along a viewing direction through the pixel. Using comparison, a value of a surface (e.g., highest or first above a threshold) is selected. In another approach, alpha blending or other projection approach combines data along the line. The volume rendered image is generated from data spaced in three dimensions rather than being of a plane in the volume. With ultrasound, real-time volume scanning may be provided, allowing display of a sequence of volume rendered ultrasound images in real time.

In another embodiment, the medical image is generated from intensities representing just a plane. A plane is scanned, and the image is generated from the scan. Alternatively, a plane is defined in a volume. The intensities from volume or 3D scanning representing the plane are used to generate the medical image, such as with MPR. Interpolation may be used to determine the intensities on just the plane from the volume data set.

In act 64, a user input device receives a position of a measurement caliper on the medical image. The processor receives the position from the user input device. For example, in FIG. 2, the user places a caliper 42 or measurement indication on the volume rendered image 38 using the user input device. The user positions the caliper 42 at the desired location for measuring. Once positioned, the user activates the measurement caliper, such as by depressing a button (e.g., clicking a mouse).

Figure 2:
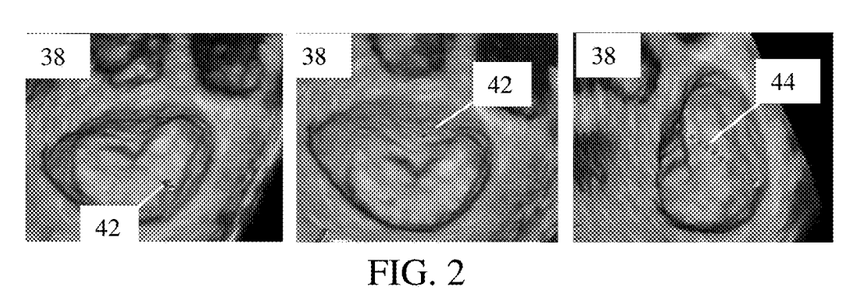
FIG. 2 shows examples of volume rendered medical images with points defined for distance calculation.

The input device provides a user selected measurement location on the displayed medical image, such as a rendered volumetric image of the three-dimensional object. For volume rendering, the location on the screen corresponds to a range of possible depths relative to or along the viewing direction of the volume rendered image. The point in three-dimensions is indeterminate based on the user selection of a 2D position on the volume rendered image 38. The user input position may also not be precise. For 2D imaging, the location corresponds to a range of possible landmark or boundary locations near to the user entered location. The user input position may not be precise.

The positions of more than one caliper 42 may be received. For a distance measurement, the positions of two or more calipers 42 (e.g., left two images of FIG. 2) or measurement shapes (e.g., oval or box) are received, and a graphic 44 linking the two positions may displayed. The graphic 44 is displayed after the identification of act 68 and/or calculation of act 72. For area or volume measurements, three or more caliper positions 44 may be received. For example, the user traces a boundary, such as a blood/tissue boundary.

In act 66 of FIG. 1, the image processor defines a ray extending from the position of each measurement caliper. The ray extends in one direction (i.e., begins at the position) or multiple directions (i.e., extends through the position). The user input position determines a point on the ray.

The length of the array is set as a default. The length may be based on the imaged area or volume, such as extending to an edge of the field of view. The ray may terminate a given distance from the caliper position 44. Any length may be used.

The direction of the ray is based on the type of imaging. For a 2D image or image representing just a plane, the ray is within the plane. A plurality of rays with any angular spacing are defined through or from the caliper position. For example, four, eight, or sixteen rays extending in one or multiple directions are defined. Alternatively, one or more rays extend out of the plane, such as where a volume scan is performed and used for generating the planar image (e.g., MPR). In other alternatives, a single ray is formed, such as along a view direction of a volume rendering displayed with the 2D MPR image on which the user positions the caliper.

For a volume rendered medical image, a single ray is defined along one direction. The ray extends along a view direction. The ray is defined along the view direction from or through the position of the caliper 44. The ray extends in one or two directions from the position. For example, the ray is cast with the position centered along the ray or the ray extending beyond the position in opposite directions. The view direction from the 3D rendering of the volume rendered image defines the direction of the ray. The mouse position and camera position provide the view direction and pixel or location in the volume for the ray casting. The ray is traced along the camera direction, towards the volume, like ray casting when rendering a 3D volume visualization. Alternatively, multiple rays are formed, such as rays with different angular spacing diverging from the camera or parallel rays with a center ray at the normal to the camera or projection plane from the user selected pixel.

One or more rays are defined for each user selected position. Where a landmark is being located, a single user selected position may be received. Where a distance is being measured, two user selected positions may be received. Where an area or volume is being measured, two (e.g., fit area shape defined by two locations), three (e.g., fit volume or area shape defined by three locations), or more (e.g., user tracing of a boundary) are received. In addition, these shapes may be refined in a subsequent step. Rays are defined for each of the user input positions. Rays may be defined for other positions, such as locations interpolated between user input positions. The defining of rays is repeated any number of times.

The ray defines a sub-set of the scan data. For example, the ray defines a line in a plane or volume. The ultrasound intensities include intensities along the line or that may be formed by interpolation to be along the line. Alternatively, the ray defines the sub-set of scan data in a cylinder, cone, or other shape about the ray. Rather than using just intensities along the ray, intensities along parallel rays or within a given distance from the ray are used.

The intensities along the line or in the sub-set may represent a boundary or other landmark. In act 68, the image processor identifies a location along the ray. Where there are multiple rays, the image processor identifies a location along one of the rays, so also identifies a specific ray. Where the ray defines a volume or area sub-set including locations within a distance from the ray (i.e., sub-region limited to be around and include the ray), the image processor identifies a location in the area or volume.

For each user input position and corresponding ray or rays, a location is identified. The identification is repeated for each position received from the user input.

Where multiple rays are defined for a given position, a location along each ray is found. The location closest to the user entered position is then selected. For rays in a plane, the ray and corresponding location of a boundary or landmark closest to the user entered position is selected. The search for the location runs along concentric rays around the clicked point. For a ray cast through a volume, the user position has no defined depth. Instead, a first boundary or landmark along the view direction or ray from the camera position is located. The location in three-dimensions is identified at the user entered position in two dimensions and a depth. A point on the volume rendered view of the 3D volume below the mouse pointer, where the volume appears opaque to the user, is identified.

The location is identified based on the intensities (e.g., medical scan data). Intensities from the ray or a sub-region around and including the ray are used to identify. Other information may alternatively or additionally be used, such as gradients calculated from the intensities, scan data from other modalities, and/or clinical information (e.g., age, sex, weight, and/or blood biomarker values).

The intensities for the displayed image (i.e., display values) or intensities from other points in the processing chain are used. For example, intensities from detected ultrasound data prior to scan conversion (i.e., in a polar or spherical coordinate scan format) are used. In another example, intensities in a Cartesian coordinate format (i.e., scan converted) prior to mapping to display values are used. The intensities may or may not be subject to dynamic range and image gain mapping.

In one embodiment, a threshold is used to identify the location. Starting from the user selected point for a 2D medical image or from the camera position for a 3D rendered image, the intensities are examined. Each intensity is compared to a threshold. The location of the first intensity above the threshold is identified. The closest intensity above the threshold is identified. The intensities may be low pass filtered or the location may be where a given number of adjacent intensities are above the threshold. Exceeding the threshold identifies the location. Alternatively, falling below a threshold identifies the location.

In one embodiment, the intensities are used to establish an opacity. Volume rendering techniques are used to identify the location. While traversing the volume along the ray, voxel values are mapped using a transfer function (e.g., to match the actual volume visualization). Any image gain and dynamic range are used to adapt to the visualization settings of the renderer, similar to volume rendering. The voxels along the ray are integrated until reaching a predefined threshold corresponding to an opaque volume surface. The space is traversed "starting from the screen" (i.e., along normal of the "near plane" of the view frustum starting from the clicked point in world coordinates) towards the volume. Without integration, volume intensities are sampled until exceeding a certain intensity threshold.

In another embodiment, a machine-learnt classifier identifies the location. Instead of using volume intensities directly, learning based methods are used to robustly determine the location form the intensities. The intensities and/or input feature values derived from the intensities (e.g., Haar wavelets) are input to a machine-learnt classifier. In another embodiment, the intensities are convolved with a Hessian-of-Gaussian or other filter kernel to determine discriminant points in the image. The results of the convolution are input to the classifier. The information from the sub-region defined by the ray or rays in provided to the machine-learnt classifier.

The classifier, based on the input feature vector, outputs an identification of the location. The depth, landmark, and/or boundary point are identified by application of the machine-learnt classifier. For example, a depth along the ray is identified with a machine-learnt classifier based on input of ultrasound data from a sub-region of the volume limited to be around and include the ray.

To speed application of the classifier, the sub-region is used. Rather than attempting to segment a whole organ or part of an organ from a field of view, the sub-region based on the defined ray limits the search region. For example, the sub-region is less than 5% of the scanned volume. This may allow for more rapid identification of the landmark, boundary, or other location. Since the search region is limited, the machine-learnt classifier may be trained to identify the location regardless of specific organs. One classifier may be trained to find a boundary without being specific to a part of an organ or even an organ. This generalization may avoid time consuming organ specific training and importantly generalizes the applicability of the technique to arbitrary organs and landmarks. In alternative embodiments, the machine-learnt classifier is organ, tissue, or part specific.

In one example, the machine-learnt classifier is trained to identify a depth along a view direction from ultrasound data and/or gradients from the ultrasound data for the sub-region. The training is to find points along boundaries of organs, such as an intra-cardiac blood pool boundary. Volume gradients and intensities are combined into a combined feature vector. A classifier, such as a probabilistic boosting tree, support vector machine, neural network, Bayesian network, or deep neural network, is trained with these features from a collection of different annotations (i.e., training data from heart chamber and/or valve scans of patients with ground truth—known locations). Where the classifier is to be generic to different organs or scanning applications, the training data includes samples from the different organs and/or scanning applications. Once trained, the classifier evaluates data for a given patient along the casted ray at runtime.

In another example, the machine-learnt classifier is trained to find nearby anatomical landmarks. Based on a user input in a general or imprecise location on a planar or volume rendered image and the resulting defined ray or rays, the classifier is used to "snap" onto a landmark, such as mitral trigones, heart valve commissures, mitral annulus, myocardial apex, pulmonary veins, LAA orifice, or a point for a closest boundary.

The machine-learnt classifier may be a matrix or matrices. Given values of an input feature vector, the classifier is trained to output the location. For example, providing intensities spatially cropped to the ray-defined sub-region to a trained neural network, the neural network convolves filter kernels with the input and/or results of other convolutions and determines a location from results of the convolutions. The output may be a map of probabilities (e.g., a heat map) where the location is selected based on the map, such as selecting a location with a greatest probability or selecting a location centered in a region of greater probabilities.

In one embodiment, deep learning is used, such as training a deep image-to-image neural network. Rather than training based on a programmer established input feature vector, the training learns filter kernels for convolution with input intensities and/or other data. Alternatively, a 3D extension of SegNet or other deep learning technique may be used. A neural network learns features and learns to find the location based on the learnt features.

In another embodiment, deep reinforcement learning is applied. A series of image processing acts are learned through reinforcement. The classifier learns to perform acts to identify the location. An artificial agent learns how to find the landmarks through reinforcement.

While stepping along rays to find blood-tissue interfaces, a classifier evaluates the input feature vector for respective sampling locations in the volume or plane. In this way, the identification is more robust against noise, artifacts, or dropout than comparison to a threshold. The training may incorporate context at different resolutions around the respective point or ray neighborhood. The trained classifier then outputs nearby landmark points by scanning over the neighborhood of the sampling locations.

For finding a boundary in three-dimensions, the user may place a plurality of positions on a volume rendered image. The boundary locations are then found by applying a machine-trained classifier based on input limited to the ray neighborhood. A mesh may then be fit to the identified locations using the intensities and the identified locations.

Figure 4:
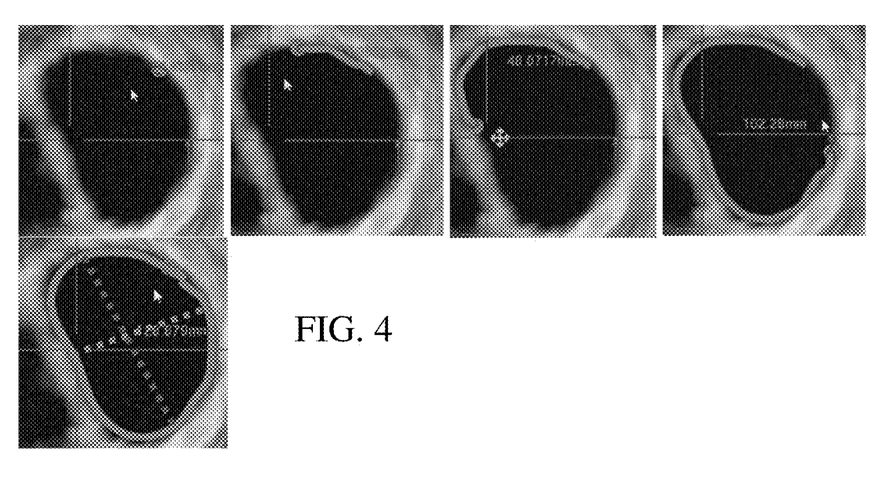
FIG. 4 shows an example sequence for manual tracing a boundary in a medical image.

For contouring in a 2D image, the locations for the contour are identified. FIG. 4 shows an example on an MPR image. The user places the cursor and then traces around the boundary, which is a blood tissue boundary in this example. The upper row of images shows manual tracing progressing in sequence from left to right. The image processor then uses the locations of the cursor to identify close locations of the actual boundary. By searching for nearby borders of a cavity (e.g., casting rays within the MPR plane and determining organ or blood pool boundary locations), the user may just "scribble" around the vicinity of the desired structure instead of meticulously tracing. The actual contour is determined based on high intensities proximal to mouse pointer. The mouse pointer is not directly hovering on the border of the cavity rather moved along its proximity, thus eliminating the need to meticulously trace. The lower image of FIG. 4 shows measurements of the contour overlaid on the image, such as contour length or minimum and maximum diameters of the curve.

For any purpose, the location in 2D or 3D is determined based on intensities and the user input of a position. The location may be based on user input on a volume rendered image where the depth for a given pixel may be ambiguous. The location may be based on user input on a volume rendered image or a 2D image representing just a plane where the user input is imprecise, allowing easier selection. The image processor identifies the location based on the intensities and the user input position.

In act 70 of FIG. 1, the image processor tracks the identified 2D or 3D location through a sequence. For example, the position and depth (i.e., 3D point) is tracked through ultrasound data of the images of the sequence. Rather than repeating the user input and corresponding ray definition and location identification, tracking is used.

Any tracking may be used, such as speckle tracking, machine-learnt classification based on tracking from one image to another, or any other tracking of a given location or region over time. Each point is tracked separately or the tracking includes a simultaneous solution for multiple points being tracked. The tracking is through the data sets representing the patient over time. This tracking may account for transducer and/or patient motion, dynamically updating the identified locations over time or as new data sets are acquired by scanning.

For instance, in the case of a MitraClip intervention, the image processor identifies a location of a puncture site in act 68. This location is tracked over time as new data sets representing a volume of the patient are acquired. Similarly, a tip of a delivery catheter is located. Based on tracking the tip also, a distance may be continually or regularly updated between the two locations.

In the case of real-time landmark tracking, the location identification technique may enhance the user experience for placing landmarks on an image in real-time. Once the mouse cursor is hovering over an MPR, the closest boundary of an organ or cardiac blood pool may be determined. Once determined, this boundary location may then be immediately tracked over time. The location may be corrected in a later image by moving the mouse pointer and activating the point, thus updating the starting position to track the landmark in that later image. The tracking then proceeds from the location identified by ray casting from the new input position. Alternatively, the location identification is repeated rather than tracking. In yet other alternatives, the location is identified for a given time or phase and not for other times or phases.

In act 72, the image processor calculates a quantity as a function of the location. The 2D or 3D location is used for a measurement or other quantification. For example, the 2D position input by the user on a volume rendering plus the depth identified in act 68 is used for quantification. In another example, a 3D point identified in act 68 based on user input to define a region for searching is used for quantification.

Any quantity may be calculated. For example, a distance between two end points is calculated. By placing calipers at different locations in tissue, a distance between the locations is measured. A size of a lesion, a length of a fetus, a width or length of a bone, or dimension of other anatomy may be measured. The user may identify the locations in a volume rendered image instead of a MPR. As another example, an area, circumference, volume, or other spatial measure is performed.

The processor uses the defined point or points for calculating. For distance, the distance between two end points positioned in the volume is calculated. The spatial extent of the volume or size of voxels is known from the scan geometry. By defining two end points in three-dimensional space, a distance between the points is calculated. The distance is in reference to three-dimensional space rather than being a distance between points in two dimensions. In some embodiments, both points may be on a same plane. The processor-assisted location identification in the plane allows for less precise and thus easier placement of the points.

For area, volume, circumference, or other measures, more than two points may be identified. The user may indicate the locations in three-dimensional space for seeds. The processor performs boundary detection, such as using thresholding, random walker or gradient processing, using the seed points to identify the boundary used in the calculation. Curve or shape fitting using the identified locations and the intensity data may be used to calculate a quantity for the fit curve or shape.

A spatial aspect of the three-dimensional object represented by the ultrasound data is measured. The measurement is based on one or more locations input on a medical image and placed more specifically by image processing the intensities.

Figure 3:
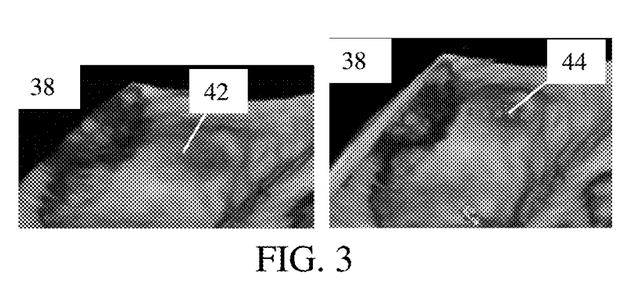
FIG. 3 shows other examples of volume rendered medical images with points defined for distance calculation.

FIGS. 2 and 3 show calculating a distance as the quantity. The user selected positions at the caliber 42 on the volume rendered image 38 are used to identify a depth (i.e., find a 3D point). Since the camera angle is set so that the user visualizes the location of interest, finding the boundary along the ray line finds the depth of interest. After placing two points with or without re-orienting the view between placement of the points, a distance is calculated. In the example of FIG. 2, the distance is the diameter of the mitral annulus AP (i.e., minor axis). In the example of FIG. 3, the distance is the LAA ostium diameter.

Figure 5:
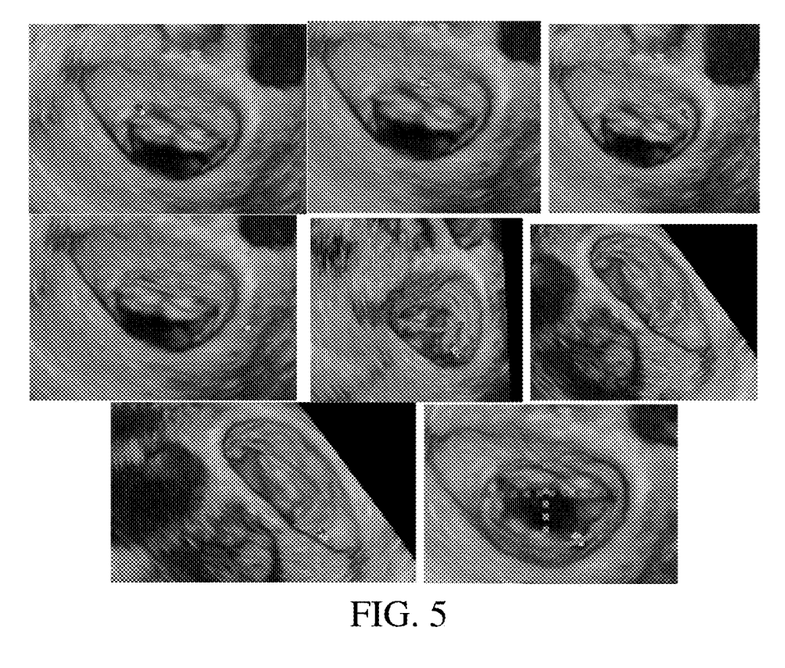
FIG. 5 shows an example of contouring with different renderings of a volume.

FIGS. 4 and 5 show calculating based on a boundary. A dimension of an area or volume (e.g., diameter), area, volume, and/or other quantity is calculated from the boundary. The boundary is based, at least in part, on identification of the point in 2D or 3D. In the example of FIG. 4, the user traces a boundary in a 2D image to calculate minor and major axes. In the example of FIG. 5, the user traces a contour of a non-planar structure represented in a volume rendering. The top two rows of images and the left image in the bottom row show cursor placements to indicate positions on the virtual rendering. The virtual rendering may be rotated for placement of some of the positions. For each position, a 3D point is located based on intensities. A curve is fit to the points or interpolated from the points. For example, a Hermite spline is formed. The curve forms the contour. In this example, the contour is for the mitral annulus. The quantity is calculated from the contour, such as measuring the length or circumference, area, minimum diameter, and/or maximum diameters of the contour. In other examples, a mesh is fit to define a 3D boundary, allowing calculation of a volume.

In alternative embodiments, a quantity is not calculated. Instead, a landmark or boundary is identified for visual inspection.

In act 74 of FIG. 1, the image processor outputs the quantity. The quantity is output to a display, such as adding the quantity to a display plane memory or buffer read by a display device. Other outputs include output to a printer, to a memory, or over a network.

The quantity is displayed adjacent to, on, or separate from the volume rendered or 2D medical image. For example, the distance between two calipers 42 is displayed over the tissue representation of the volume rendered image or in the background but not over the tissue representation. Where a real-time sequence of images is presented, the quantity may be shown on an image or images generated after the image used to indicate one or more locations. The quantity is displayed on the subsequent image. The corresponding locations for that data set may be tracked or independently identified.

The quantity is output as a textual or numerical value. In other embodiments, the quantity is output in a graph, chart, waveform, spreadsheet, or other indicator of the quantity. The quantity as a function of time may be output to show variation over a heart cycle or other period. The quantity may be output by itself or in combination with other values.

For example, the measurement over time or a sequence of volume datasets through a heart or breathing cycle is output. As another example, the quantity is output with other quantities representing the norm, deviation, or abnormal results. Other outputs on the medical image may be provided, such as the graphic representation of the measurement being made (e.g., dashed line between endpoints for a distance measure or a contour or mesh for area or volume related measurements).

Other display variation may be performed. For example, after identifying the 3D point in a volume, orthogonal MPRs may be aligned to the point. The MPRs are centered at the point, allowing the user to verify that the image processor has identified the desired point given the user's general or inaccurate caliper positioning.

Multi-modality imaging guidance may provide for enhanced procedural workflow and outcomes. In the case of the MitraClip deployment as a minimally invasive therapy, fluoroscopy is used for guiding the delivery catheter and the device deployment while ultrasound 3D TEE or volume ICE is used to guide trans-septal puncture and positioning of the device or delivery catheter before deployment. Fluoroscopy is a 2D projection that provides good visualization of the delivery catheter and device.

The measurement or quantity from one mode (e.g., ultrasound) may be registered with another mode (e.g., fluoroscopy) of medical imaging. For example, the position and orientation of the ultrasound transducer is detected in a fluoroscopy image. This detection is used to spatially align or register the coordinate systems. As a result, a location in the fluoroscopy projection may be determined from the location in the ultrasound. The locations and/or quantities may then be overlaid as graphics on the fluoroscopy image. For example, a distance to the trans-septal puncture site from the tip of the deliver catheter and the location of the trans-septal puncture site determined from ultrasound are overlaid on the fluoroscopy image to assist in navigating the delivery catheter.

After trans-septal puncture is done, the delivery catheter is advanced into the left atrium pointing towards the targeted anatomy. In a next step, the closure device is inserted and advanced to the tip of the delivery catheter. The distance between the closure device and the location for deployment is calculated and output. Once the closure device reached its optimal distance to the puncture site as determined from ultrasound, the system shows a corresponding message overlaid on the fluoroscopy image. The distance may be color coded to indicate relative range or proper position, such as green in case it is greater than 4 mm, otherwise red if below 3.5 mm, and yellow if between 4 and 3.5 mm. Once at the desired distance, the closure device may then be deployed fully using fluoroscopy or a combination of fluoroscopy and 3D TEE or volume ICE.

Figure 6:
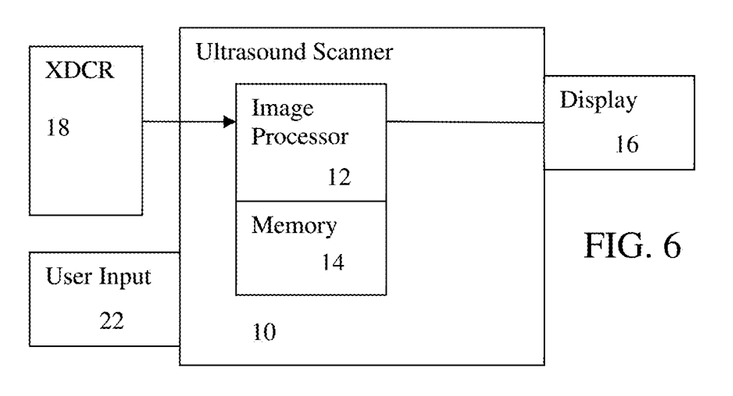
FIG. 6 is a block diagram of one embodiment of a system for measurement point determination.

FIG. 6 shows a medical diagnostic imaging system 10 for measuring in medical imaging. The system 10 is a medical diagnostic ultrasound imaging system, but may be a computer, workstation, database, server, or other imaging system. Other medical imaging systems may be used, such as a computed tomography or a magnetic resonance system.

The system 10 implements the method of FIG. 1 or a different method. The system 10 provides a measurement tool on the medical image. Using the system 10, clinicians may measure the anatomy of interest and evaluate the relative position of the structures with accurate measurements between points defined in three-dimensional or two-dimensional space despite the user inputting an inexact location on the image or depth ambiguity for input on volume rendered images. The point or points are found in real time or quickly by finding the desired location based on user input of a proximate location.

The system 10 includes a processor 12, a memory 14, a display 16, a transducer 18, and a user input 22. Additional, different, or fewer components may be provided. For example, the system 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the system 10 does not include the transducer 18.

The transducer 18 is a piezoelectric or capacitive device operable to convert between acoustic and electrical energy. The transducer 18 is an array of elements, such as a one-dimensional, multi-dimensional, or two-dimensional array. For example, the transducer 18 is a TEE, TTE, or an ICE probe. Alternatively, the transducer 18 is a wobbler for mechanical scanning in one dimension and electrical scanning in another dimension. In other alternatives, the transducer 18 is a one-dimensional array.

The system 10 uses the transducer 18 to scan a volume or a plane. Electrical and/or mechanical steering allows transmission and reception along different scan lines. Any scan pattern may be used. In one embodiment, the transmit beam is wide enough for reception along a plurality of scan lines, such as receiving a group of up to sixteen or more receive lines for each transmission. In another embodiment, a plane, collimated or diverging transmit waveform is provided for reception along a plurality, large number, or all scan lines.

Ultrasound data representing a plane or a volume is provided in response to the scanning. The ultrasound data is beamformed by a beamformer, detected by a detector, and/or scan converted by a scan converter. The ultrasound data may be in any format, such as polar or Cartesian coordinates, Cartesian coordinate with polar coordinate spacing between planes, or another format. In other embodiments, the ultrasound data is acquired by transfer, such as from a removable media or over a network. Other types of medical data representing a volume may also be acquired.

The memory 14 is a buffer, cache, RAM, removable media, hard drive, magnetic, optical, or other now known or later developed memory. The memory 14 may be a single device or group of two or more devices. The memory 14 is shown within the system 10, but may be outside or remote from other components of the system 10.

The memory 14 stores the ultrasound data and/or location information. For example, the memory 14 stores flow or tissue motion estimates (e.g., velocity, energy or both) and/or B-mode ultrasound data. The medical image data is a two or three-dimensional data set (e.g., data representing acoustic response from locations distributed in three dimensions (nxmxo where n, m and o are all integers greater than 1)), or a sequence of such sets. For example, a sequence of sets over a portion, one, or more heart cycles of the heart are stored. A plurality of sets may be provided, such as associated with imaging a same patient, organ or region from different angles or locations. The data represents a volume or plane of a patient, such as representing a portion or all the heart.

For real-time imaging, the ultrasound data bypasses the memory 14, is temporarily stored in the memory 14, or is loaded from the memory 14. Real-time imaging may allow delay of a fraction of seconds, or even seconds, between acquisition of data and imaging. For example, real-time imaging is provided by generating the images substantially simultaneously with the acquisition of the data by scanning. While scanning to acquire a next or subsequent set of data, images are generated for a previous set of data. The imaging occurs during the same imaging session used to acquire the data. The amount of delay between acquisition and imaging for real-time operation may vary. In alternative embodiments, the ultrasound data is stored in the memory 14 from a previous imaging session and used for imaging without concurrent acquisition.

For measurement, only one dataset may be used. Only one dataset or scan of a volume or plane is acquired, or one is selected from a sequence, such as using a "freeze" operation. Alternatively, the measurements are made while real-time imaging is provided. The measurement over time is determined.

The memory 14 is additionally or alternatively a computer readable storage medium with processing instructions. The memory 14 stores data representing instructions executable by the programmed image processor 12 for measurement point determination. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The user input device 22 is a button, slider, knob, keyboard, mouse, trackball, touch screen, touch pad, combinations thereof, or other now known or later developed user input devices. The user may operate the user input device 22 to set rendering values (e.g., define a clip plane, select a type of rendering, or set an offset angle), select MPR plane arrangements, alter a position of one or more planes, select a measurement location on a medical image, and/or operate the system 10. For example, the user input device 22 receives from the user an indication of a position on a medical image, such as a volume rendered image. A plurality of such measurement locations may be received. As another example, the user input device 22 receives user indication of a view direction for volume rendering and/or position of one or more MPRs.

The image processor 12 is a general processor, digital signal processor, three-dimensional data processor, graphics processing unit, application specific integrated circuit, field programmable gate array, digital circuit, analog circuit, combinations thereof, or other now known or later developed device for processing medical image data. The image processor 12 is a single device, a plurality of devices, or a network. For more than one device, parallel or sequential division of processing may be used. Different devices making up the processor 12 may perform different functions, such as a volume rendering graphics processing unit and a control processor for calculating measurements operating separately. In one embodiment, the image processor 12 is a control processor or other processor of a medical diagnostic imaging system, such as the medical diagnostic ultrasound imaging system 10. In another embodiment, the image processor 12 is a processor of an imaging review workstation or PACS system. In yet another embodiment, the image processor 12 is a volume rendering processor.

The image processor 12 is configured by hardware, firmware, and/or software. For example, the image processor 12 operates pursuant to stored instructions to perform various acts described herein, such as acts 62, 64, 66, 68, 70, 72, and 74 of FIG. 1.

In one embodiment, the image processor 12 is configured to display a medical image and receive user input of a location on the medical image based on a user interface. For example, a MPR and/or a volume rendering of the volume of the patient is generated from the ultrasound data. Any type of volume rendering may be used, such as projecting along ray lines from a view point or in a view direction. Lighting, transfer function, or other volume rendering operations may be provided.

The image processor 12 is configured to cast a ray from the position along a view direction or cast rays from the position in a plane. The image processor 12 is configured to select a location along or around the ray based on ultrasound data from the scan of the volume or plane. The selection uses ray casting, a rendering transfer function, thresholding, and/or application of a machine-learnt classifier. For example, ultrasound data in a sub-volume defined by the cast ray is input to a machine-learnt classifier, which responsively outputs the location within the sub-volume or locations restricted to be on the ray.

The image processor 12 is configured to generate a graphic indicating a point. For example, the 3D point at the user input position and the image processor 12 determined depth or location is marked in the image. Graphics for calculated quantities based on the selected location may be generated. The graphic is a dash polyline or other indicator of the measurement locations relative to the medical image.

The image processor 12 is configured to calculate a value as a function of the 2D or 3D point. Using the measurement locations, the processor 12 calculates a value, such as a distance. The quantity may be output with the image to the display 16.

The display device 16 is a CRT, LCD, plasma, monitor, projector, printer, or other now known or later developed display device. The display 16 is configured by loading an image from the processor into a display buffer. Alternatively, the display 16 is configured by reading out from a display buffer or receiving display values for pixels.

The display 16 is configured to display a medical image (e.g., a volume rendering), clip plane navigation user interface, MPR images, plane graphics, calipers, measurement graphics, and/or user interface tools. The volume rendering is displayed by itself or in combination with images of planes. Multiple images may be displayed in different portions of a screen of the display 16, such as in different windows. The display 16 is configured to display a graphic and/or a value, such as a quantity calculated in measuring.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for measurement point determination in imaging with an ultrasound scanner, the method comprising:
   displaying, on a display, an ultrasound image three-dimensionally rendered from ultrasound data representing a three-dimensional volume of tissue of a patient, the three-dimensionally rendered image being a two-dimensional representation of the three-dimensional volume rendered along a view direction;
   receiving, from a user input device, a position on the three-dimensionally rendered, displayed ultrasound image of a measurement caliper;
   defining a ray along the view direction of the three-dimensionally rendered, displayed ultrasound image from the position on the three-dimensionally rendered, displayed ultrasound image of the measurement caliper into the three-dimensional volume, the ray extending from the position into the volume out of a plane of the two-dimensional representation;
   identifying a depth along the ray with a machine-learnt classifier based on input of ultrasound data from a sub-volume of the volume, the sub-volume limited to be around and include the ray;
   calculating, by an image processor, a quantity as a function of the position of the measurement caliper and the depth; and
   outputting the quantity.

2. The method of claim 1 wherein displaying comprises displaying the ultrasound image as a volume rendered cardiac image in a sequence of images; and
   further comprising tracking the position and depth through ultrasound data of the images of the sequence.

3. The method of claim 1 wherein receiving comprises receiving an activation of the measurement caliper.

4. The method of claim 1 wherein defining the ray comprises ray casting with the view direction being a view direction from the three-dimensional rendering.

5. The method of claim 1 wherein identifying the depth comprises identifying the depth with intensities from the ultrasound data and gradients from the ultrasound data for the sub-volume.

6. The method of claim 1 wherein identifying the depth comprises identifying the depth with the sub-volume comprising less than 5% of the volume.

7. The method of claim 1 wherein identifying the depth comprises identifying the depth with the ultrasound data in a polar coordinate scan format.

8. The method of claim 1 wherein identifying the depth comprises identifying the depth with the machine-learnt classifier comprising a probabilistic boosting tree or deep neural network learnt classifier.

9. The method of claim 1 wherein identifying the depth comprises identifying the depth with the machine-learnt classifier trained from samples of different organs.

10. The method of claim 1 wherein calculating comprises calculating a distance as the quantity, the position and point defining an end of the distance in the volume.

11. The method of claim 1 wherein calculating comprises calculating an area, volume, or dimension of the area or volume with the position and point defining a point in three-dimensions of a boundary of the area or volume.

12. The method of claim 1 wherein outputting the quantity comprises displaying the quantity adjacent to or on another ultrasound image rendered subsequently to the ultrasound image.

13. A method for measurement point determination in imaging with a medical scanner, the method comprising:
- displaying, on a display, a medical image mapped from intensities representing tissue of a patient;
- receiving, from a user input device, a position on the medical image of a measurement caliper;
- defining a ray in response to the receipt of the position on the medical image, the ray defined to extend from the position of the measurement caliper;
- identifying a location along the ray based on the intensities from a sub-region limited to be around and include the ray; and
- calculating, by an image processor, a quantity as a function of the location; and
- outputting the quantity.

14. The method of claim 13 wherein displaying comprises displaying the medical image representing just a plane, wherein defining the ray comprises defining the ray as one of a plurality of rays in the plane, the ray having a boundary at the location closest to the position.

15. The method of claim 13 further comprising repeating receiving, defining, and identifying for other positions in tracing a boundary, and wherein calculating comprises calculating as a function of the boundary.

16. The method of claim 13 wherein identifying the location comprises identifying the location where the intensities along the ray transition relative to a threshold.

17. The method of claim 13 wherein identifying the location comprises identifying with input of the intensities of the sub-region to a machine-learnt classifier.

18. The method of claim 13 wherein displaying comprises volume rendering wherein the intensities comprise ultrasound data representing a three-dimensional portion of the tissue of the patient, wherein defining the ray comprises defining the ray along a view direction of the volume rendered medical image, and wherein identifying the location comprises identifying the location in three-dimensions as at the position in two dimensions and a depth based on the intensities from the sub-region around and including the ray.

19. A medical ultrasound system comprising:
- an ultrasound scanner configured to scan a volume of a patient;
- a user input device configured to receive an indication of a two-dimensional position on a displayed volume rendered image of the volume of the patient, the displayed volume rendered image being a two-dimensional distribution of pixels rendered from data representing the volume of the patient in three dimensions so that the position is a selected pixel ambiguous with respect to a third dimension of the three dimensions; and
- an image processor configured to cast a ray from the position along a view direction used to render the volume rendered image, the view direction in the third dimension, to select a location along the ray based on ultrasound data from the scan of the volume, wherein the image processor is configured to select by application of the ultrasound data in a sub-volume around and including the ray to a machine-learnt classifier, and to generate a graphic indicating a point at the position and the location.

* * * * *